US012745976B2

(12) United States Patent
Diwekar

(10) Patent No.: US 12,745,976 B2
(45) Date of Patent: Sep. 29, 2026

(54) SYSTEMS AND METHODS FOR PERSONALIZED MEDICINE IN IVF FOR REDUCED DOSAGE AND TESTING, AND BETTER OUTCOMES

(71) Applicant: Urmila Diwekar, Crystal Lake, IL (US)

(72) Inventor: Urmila Diwekar, Crystal Lake, IL (US)

( * ) Notice: Subject to any disclaimer, the term of this patent is extended or adjusted under 35 U.S.C. 154(b) by 299 days.

(21) Appl. No.: 18/198,630

(22) Filed: May 17, 2023

(65) Prior Publication Data

US 2024/0285250 A1 Aug. 29, 2024

Related U.S. Application Data

(60) Provisional application No. 63/447,689, filed on Feb. 23, 2023.

(51) Int. Cl.
*A61B 8/08* (2006.01)

(52) U.S. Cl.
CPC .................................... *A61B 8/08* (2013.01)

(58) Field of Classification Search
CPC .............. A61B 8/08; A61K 38/22; A61P 5/06
USPC ..................................................... 600/35–38
See application file for complete search history.

(56) References Cited

U.S. PATENT DOCUMENTS

| | | | | |
|---|---|---|---|---|
| 9,353,172 | B2 * | 5/2016 | Nordkild | A61K 47/60 |
| 11,679,145 | B2 * | 6/2023 | Arce | A61P 15/00 435/366 |
| 2023/0015833 | A1 * | 1/2023 | Shtraizent | G16H 20/10 |

* cited by examiner

*Primary Examiner* — Kaylee R Wilson
(74) *Attorney, Agent, or Firm* — Scherrer Patent & Trademark Law., P.C.; Stephen T. Scherrer; Monique A. Morneault

(57) ABSTRACT

The systems and methods of the present invention facilitate optimized and personalized drug treatment for in vitro fertilization patients. Moreover, the invention allows physicians to make scientific-based decision making. Specifically, the invention reduces drug dosage and testing and helps to get better outcomes.

13 Claims, 12 Drawing Sheets

Final Report

STOCHASTIC RESEARCH TECHNOLOGIES example1 REPORT

ANTAGONIST START DAY 6

DOSAGE PROFILE

| DAY | FSH+HMG(IU/DAY) |
|---|---|
| 1 | 187.50 |
| 2 | 187.50 |
| 3 | 187.50 |
| 4 | 187.50 |
| 6 | 225.00 |
| 7 | 225.00 |
| 8 | 225.00 |
| 9 | 187.50 |
| 10 | 187.50 |

No dose on trigger day
Dosage is zero after Day 10

USE THE EQUATION DOSAGE = FSH+HMG TO CALCULATE FSH AND HMG

| DAY | TYPE | FOLLICULAR SIZE DISTRIBUTION (mm) | | | | | |
|---|---|---|---|---|---|---|---|
| | | 0-4 | 4-8 | 8-12 | 12-16 | 16-20 | 20-24 |
| 1 | ACTUAL | 10.00 | 3.00 | 0.00 | 0.00 | 0.00 | 0.00 |
| 1 | MODEL | 10.00 | 3.00 | 0.00 | 0.00 | 0.00 | 0.00 |
| 5 | ACTUAL | 2.00 | 8.00 | 3.00 | 0.00 | 0.00 | 0.00 |
| 5 | MODEL | 1.08 | 6.75 | 5.14 | 000 | 0.02 | 0.00 |

OPTIMAL FOLLICULAR SIZE DISTRIBUTION

| DAY | TYPE | FOLLICULAR SIZE DISTRIBUTION (mm) | | | | | |
|---|---|---|---|---|---|---|---|
| 6 | MODEL | 0.40 | 5.02 | 6.99 | 0.59 | 0.00 | 0.00 |
| 7 | MODEL | 0.79 | 1.53 | 9.34 | 1.28 | 0.06 | 0.00 |
| 8 | MODEL | 0.28 | 0.46 | 8.71 | 3.40 | 0.14 | 0.00 |
| 9 | MODEL | 0.28 | 0.40 | 4.92 | 7.25 | 0.11 | 0.05 |
| 10 | MODEL | 0.17 | 0.15 | 1.96 | 9.23 | 1.43 | 0.06 |
| 11 | MODEL | 0.00 | 0.00 | 0.00 | 2.24 | 8.37 | 2.38 |
| 12 | MODEL | 0.00 | 0.00 | 0.00 | 0.00 | 0.00 | 13.00 |

SUGGESTED TRIGGER DAY IS DAY 11

*FIG. 20*

SYSTEMS AND METHODS FOR PERSONALIZED MEDICINE IN IVF FOR REDUCED DOSAGE AND TESTING, AND BETTER OUTCOMES

The present invention claims priority to U.S. Prov. Pat. App. No. 63/447,689, titled "Systems and Methods for Personalized Medicine in IVF for Reducing Dosage and Testing, and Better Outcomes," filed Feb. 23, 2023, which is incorporated herein by reference in its entirety.

TECHNICAL FIELD

The present invention relates to systems and methods for facilitating personalized and optimized drug treatment for in vitro fertilization (IVF) patients. Specifically, the present invention allows a physician to decide the optimal daily dosage of hormones like follicle stimulating hormone (FSH) and human menopausal gonadotropins (HMG) for the superovulation stage of IVF for patients to obtain better outcomes. Moreover, the present invention reduces total drug dosage and testing for the superovulation cycle and results in a higher number of Grade A embryos. Specifically, the invention uses first visit and second visit follicular size data from the patient, and the hormone doses used on initial days, to personalize and optimize the dosage profile for the remaining days of the superovulation cycle. Although there are hormones available from various companies, the invention can predict daily drug dosage for whatever hormone is used by the physician.

BACKGROUND

The IVF process is one of the most recommended treatments in Assisted Reproductive Technologies (ART). 1.7% of infants were born through ART in the United States in 2015. IVF is a process by which oocytes or egg cells are fertilized by a sperm outside the body in a laboratory simulating similar conditions in the body, and then the fertilized eggs or embryos are implanted back in the uterus for a full-term pregnancy. It has four basic stages: superovulation, egg retrieval, insemination/fertilization, and embryo transfer.

IVF is an expensive treatment, and the out-of-pocket costs per cycle tend to be around $15,000-$30,000 (Forbes, 2023). This cost varies and increases with multiple factors, such as unsuccessful IVF cycles, multiple births, low-birthweight infants, and preterm births occurring from IVF cycles. Superovulation is the largest portion of the cost of IVF. Currently, this step is executed using almost daily monitoring of the follicular development using ultrasound and blood tests. The daily dosage of hormones is adjusted at each visit based on these tests. The cost associated with patient monitoring and testing and the hormonal drugs makes the superovulation very expensive. Although there are general guidelines for the dosage limits, the daily dose is not individualized for each patient. IVF procedures can have side effects such as ovarian hyperstimulation syndrome (OHSS), and the remedial actions are still unidentified. Patients suffering from polycystic ovarian syndrome (PCOS) are found to be the ones most susceptible to OHSS. However, many patients who do not suffer from PCOS may also develop OHSS after stimulation. The evidence is building in support of personalized IVF treatment and tools like our invention allow optimal patient-specific drug-dosage profiles to reduce hyperstimulation, reduce the cost of treatment, and improve the oocyte and embryo quality and quantity to increase the overall success rate of IVF, resulting in successful pregnancies and live births.

SUMMARY OF THE INVENTION

This innovation is the first of its kind that offers personalized and optimized treatment for each patient for a whole IVF superovulation cycle. It is based on customized modeling for each patient using chemical engineering principles. Advanced optimization and optimal control algorithms are used to reduce total dosage, reduce testing, and improve outcomes. Clinical trial results show that with this innovation, on average total dosage is reduced by 20-40%, testing by 50 to 70%, and results in a higher number of Grade A embryos and higher pregnancy rates.

The present invention relates to systems and methods for facilitating personalized and optimized drug treatment for IVF patients. Specifically, the present invention allows a physician to decide the optimal daily dosage of hormones like FSH and HMG for the superovulation stage of IVF to obtain better outcomes for patients. Moreover, the present invention reduces total drug dosage and testing for the cycle and results in a higher number of Grade A embryos.

To this end, the present invention facilitates a method for simplifying, optimizing, and personalizing drug treatment for patients. The method comprises the steps of: providing an apparatus configured to identify and measure follicle sizes in an IVF patient; obtaining first follicle size data of the IVF patient using the apparatus at a first time; determining an initial hormone dosage for administering to the IVF patient; administering the initial hormone dosage to the IVF patient until a second time; obtaining second follicle size data of the IVF patient using the apparatus at the second time; providing a decision support tool configured to calculate an optimized drug treatment plan for the IVF patient; entering the first follicle size data of the IVF patient, second follicle size data of the IVF patient, and the initial hormone dosage administered to the IVF patient at the first time; calculating the optimal daily hormone dosage for the IVF patient using the decision support tool; and administering the optimal daily hormone dosage to the IVF patient for a cycle.

In an embodiment, the apparatus is an ultrasound machine.

In an embodiment, the method further comprises the step of: determining the initial hormone dosage for administering to the IVF patient using the decision support tool.

In an embodiment, initial hormone dosage for administering to the IVF patient is based on the age of the IVF patient, anti-mullerian hormone (AMH) data of the IVF patient, and the FSH data of the IVF patient.

In an embodiment, the initial hormone data is calculated based on heuristics.

In an embodiment, the second time is between about 4 days and 6 days after the first time.

In an embodiment, the optimal daily dosage is determined for the IVF patient for the cycle of IVF treatment.

In an embodiment, the optimal daily dosage for the IVF patient is calculated using optimal control theory.

In an embodiment, the optimized drug treatment plan for the IFV patient comprises a personalized differential-algebraic equations-based model using the first and the second follicle size distribution data of the patient and information about the initial hormone dosage.

In an embodiment, the optimal daily hormone dosage comprises a hormone selected from the group of FSH, HMG, and a combination of FSH and HMG.

In an embodiment, the decision support tool further calculates an antagonist start day.

In an embodiment, the decision support tool further calculates estrogen levels for each day of the cycle.

In an embodiment, the decision support tool further calculates expected daily follicle sizes for the cycle.

In an embodiment, the decision support tool further calculates a trigger day for the IVF patient within the cycle.

In an alternate embodiment of the present invention, a system for facilitating an optimized and personalized drug treatment for IVF patients is provided. The system comprises: an apparatus configured to identify and measure follicle sizes in an IVF patient; and a decision support tool configured to calculate an optimal daily dosage for the IVF patient using first follicle size data of the IVF patient via the apparatus at a first time, an initial hormone dosage, and second follicle size data of the IVF patient via the apparatus at a second time within a cycle.

In an embodiment, the apparatus is an ultrasound machine.

In an embodiment, the decision support tool is further configured to calculate a trigger day for the IVF patient within the cycle.

In an embodiment, the decision support tool is further configured to calculate an initial hormone dosage for administering to the IVF patient.

In an embodiment, the initial hormone dosage is calculated using a nomogram.

In an embodiment, the initial hormone dosage for administering to the IVF patient is based on the age of the IVF patient, AMH data of the IVF patient, and the antral follicle count (AFC) data of the IVF patient.

In an embodiment, the initial hormone data is calculated based on heuristics.

In an embodiment, the second time is between about 4 days and 6 days after the first time.

In an embodiment, the optimal daily hormone dosage is determined for the IVF patient for a cycle of IVF treatment.

In an embodiment, the optimal daily hormone dosage for the IVF patient is calculated using optimal control theory.

In an embodiment, the optimal daily hormone dosage comprises a hormone selected from the group of FSH, HMG, and a combination of FSH and HMG.

In an embodiment, the optimal daily hormone dosage further comprises estrogen.

In an embodiment, the decision support tool further calculates expected daily follicle sizes for the cycle.

In an embodiment, the decision support tool further calculates a trigger day for the IVF patient within the cycle.

In an alternate embodiment of the present invention, a system for facilitating an optimized and personalized drug treatment for IVF patients is provided. The system comprises: an apparatus configured to identify and measure follicle sizes in an IVF patient; and a decision support tool configured to calculate an optimal daily dosage for the IVF patient using first follicle size data of the IVF patient via the apparatus at a first time, an initial hormone dosage, and second follicle size data of the IVF patient via the apparatus at a second time.

In an embodiment, the apparatus is an ultrasound machine.

In an embodiment, the decision support tool is further configured to calculate a trigger day for the IVF patient within the cycle.

It is, therefore, an objective and advantage of the present invention to provide systems and methods for optimized care for IVF patients.

Moreover, it is an objective and advantage of the present invention to provide a scientific and easy-to-use decision-making tool for physicians.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIG. 20 illustrates an exemplary final report for a decision support tool for determining a personalized drug dosage profile for a patient in an embodiment of the present invention.

DETAILED DESCRIPTION OF THE PRESENTLY PREFERRED EMBODIMENTS

The present invention relates to systems and methods for facilitating personalized and optimized drug treatment for IVF patients. Specifically, the present invention allows a physician to decide the optimal daily dosage for the superovulation stage of IVF to obtain better outcomes. Moreover, the present invention reduces total drug dosage and testing for the cycle and results in a higher number of Grade A embryos.

The invention uses first visit and second visit follicular size data from the patient when the dosage is given to personalize and optimize the dosage profile. Therefore, although there are hormones available from various companies, the invention can predict daily drug dosage for whatever hormone is used by the physician.

Figure 1:
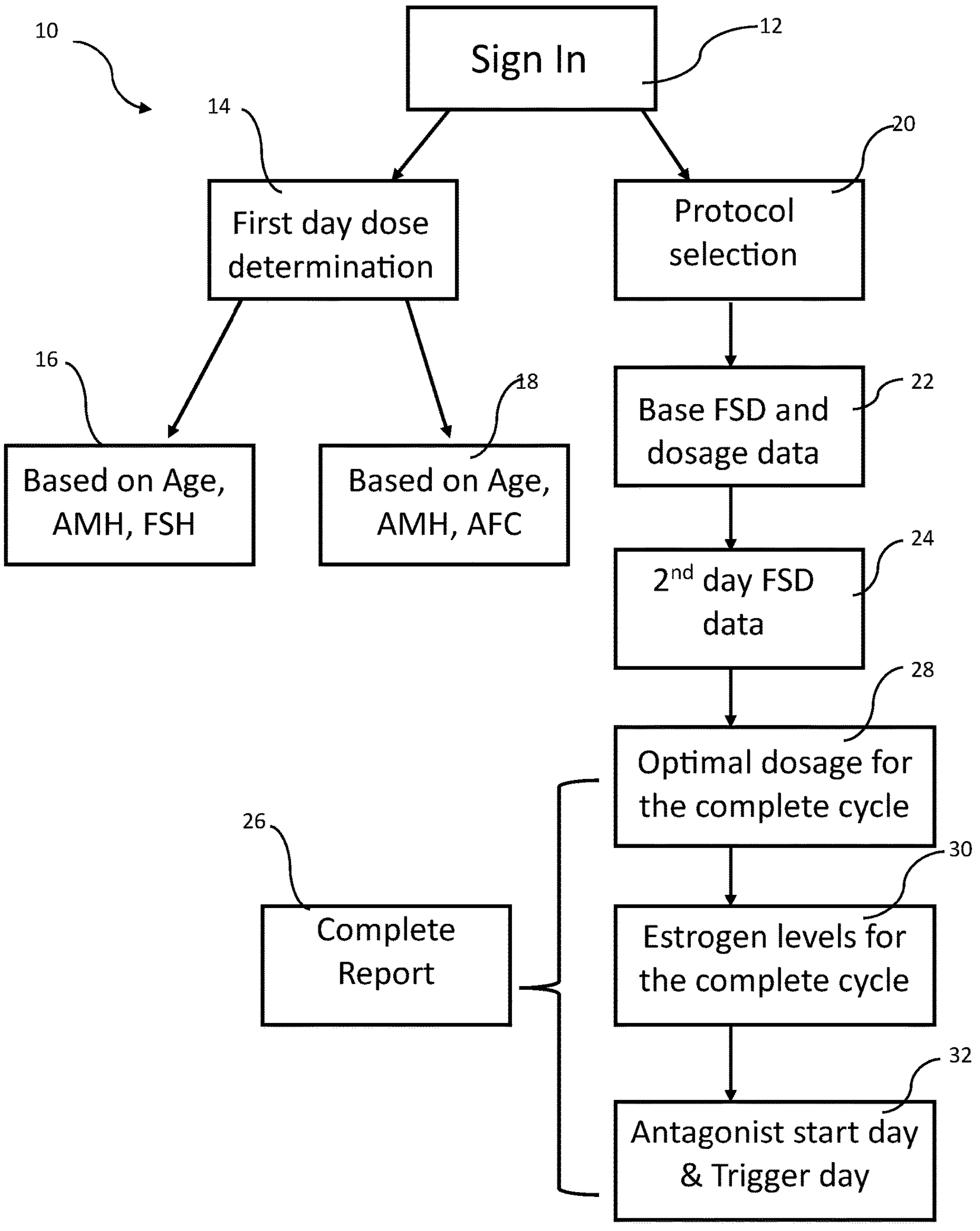
FIG. 1 illustrates an overview of the present invention's systems and methodology, showing the various steps involved in the determination of personalized drug dosage profiles for each patient in an embodiment of the present invention.

Referring now to FIG. 1, a flowchart 10 outlining steps involved in the decision support tool to guide physicians in obtaining personalized and optimized drug dosage profiles for each patient, which reduces drugs, testing, and side effects and results in a higher number of Grade A embryos. FIG. 1 provides a general description of the present invention and how a physician may utilize the present invention to provide optimal and personalized treatment for their IVF patients.

Figure 2:
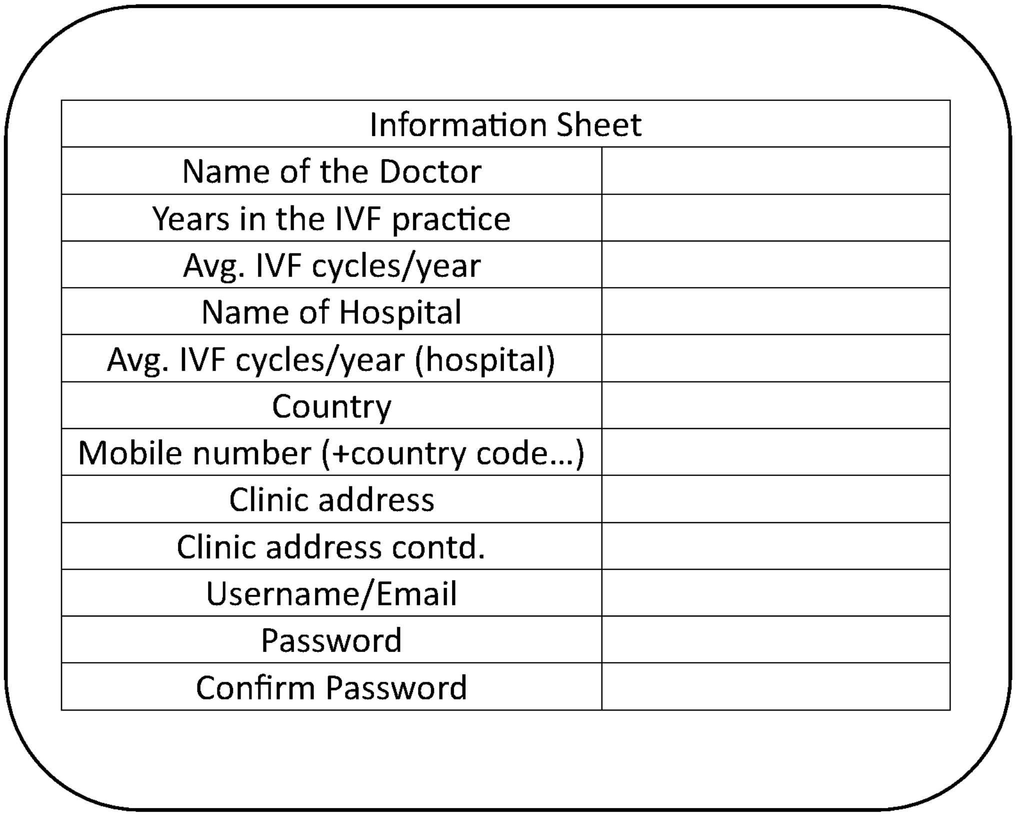
FIG. 2 illustrates a signup screen for a decision support tool for determining personalized drug dosage profiles for patients in an embodiment of the present invention.
Figure 3:
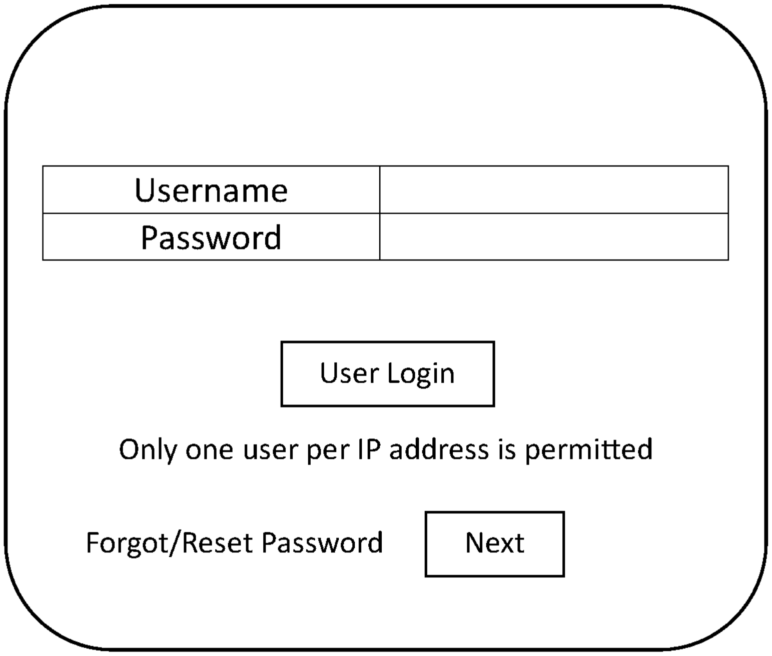
FIG. 3 illustrates a sign-in screen for a decision support tool for determining personalized drug dosage profiles for patients in an embodiment of the present invention.
Figure 4:
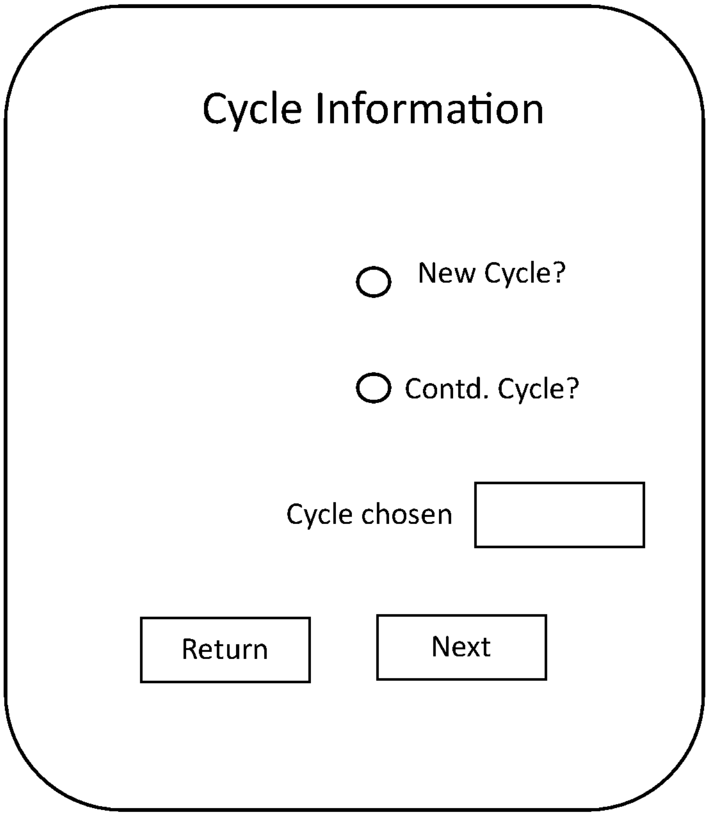
FIG. 4 illustrates cycle information screen for a decision support tool for determining personalized drug dosage profiles for patients in an embodiment of the present invention.
Figure 5A:
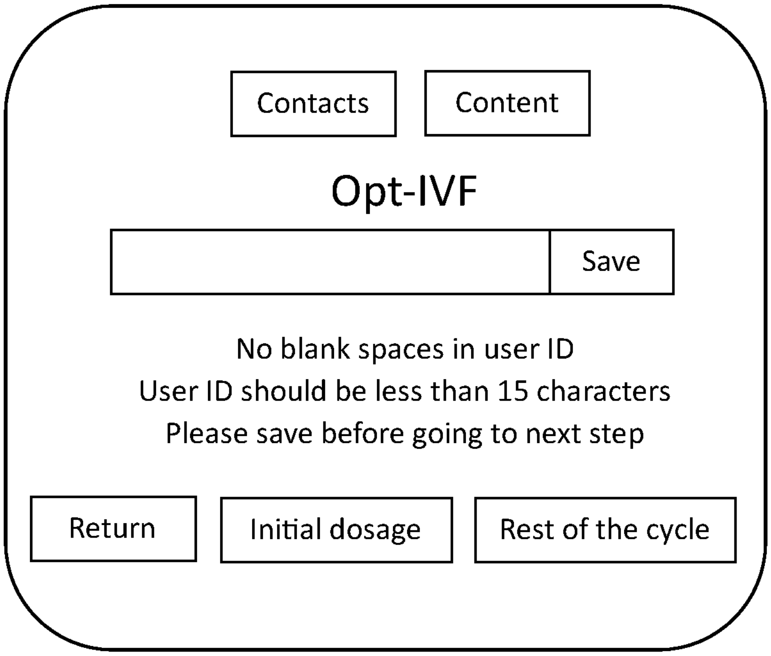
FIGS. 5A-5B illustrate a patient ID screen for a decision support tool for determining personalized drug dosage profiles for patients in an embodiment of the present invention.
Figure 5B:
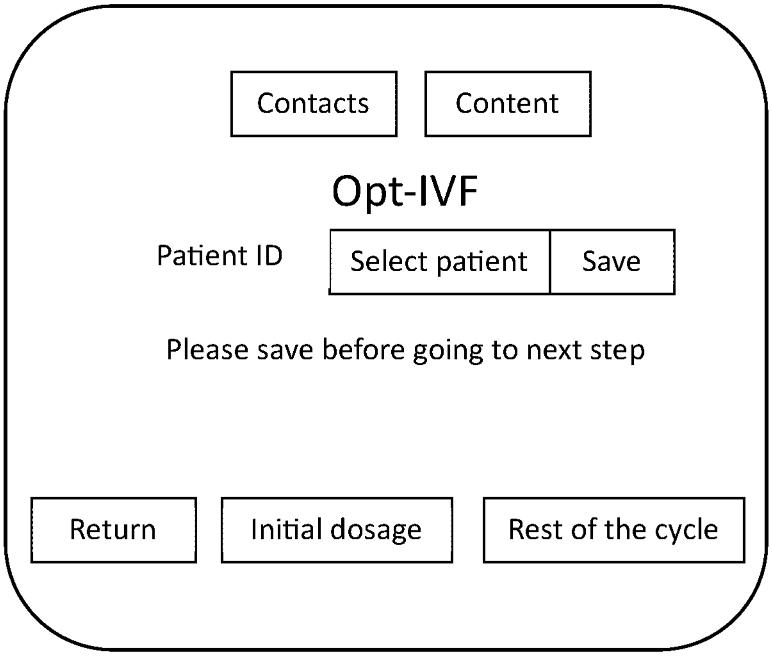
Figure 12:
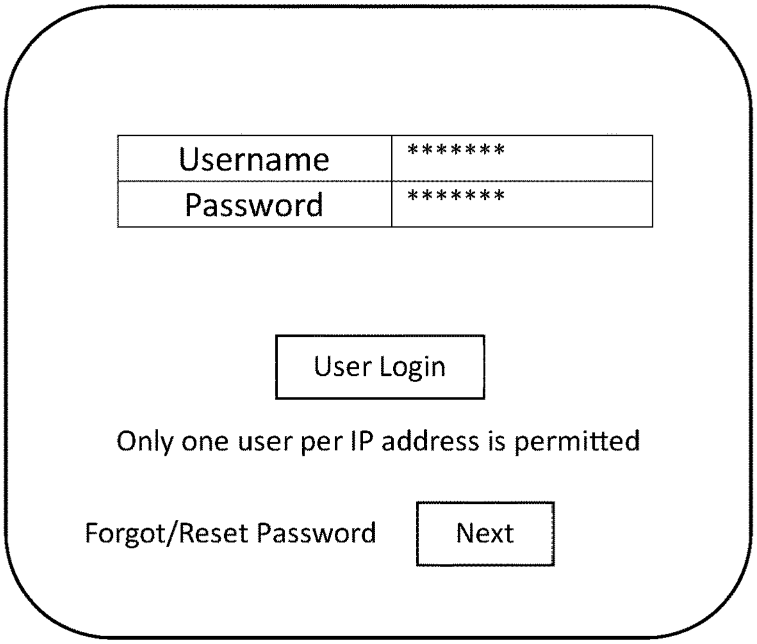
FIG. 12 illustrates an exemplary sign-in screen for a decision support tool for determining a personalized drug dosage profile for a patient in an embodiment of the present invention.
Figure 13:
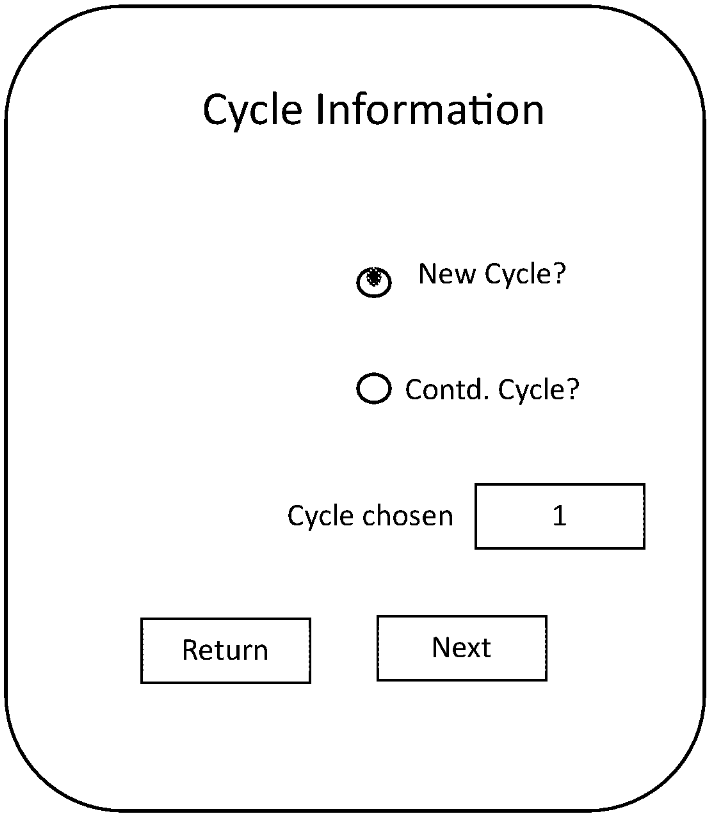
FIG. 13 illustrates an exemplary new cycle selection screen for a decision support tool for determining a personalized drug dosage profile for a patient in an embodiment of the present invention.
Figure 14:
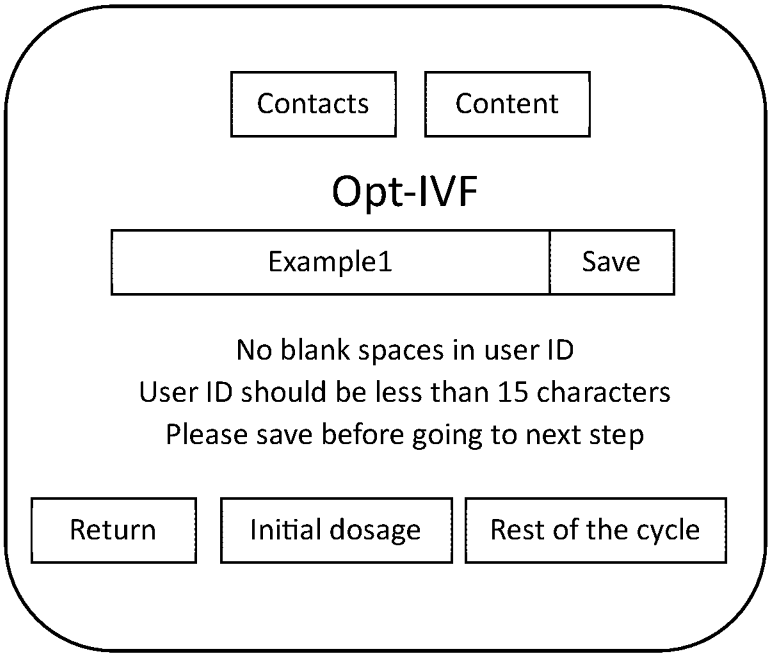
FIG. 14 illustrates an exemplary patient ID saving screen for a decision support tool for determining a personalized drug dosage profile for a patient in an embodiment of the present invention.

The physician has to sign up or sign-in on the web to use the invention via step 12. Using a signup email address and password, he/she can enter the system. Example sign up and sign-in screens are illustrated in FIGS. 2, 3, and 12. The signup or sign-in protocol may also request information concerning cycle information (whether a new cycle or a continued cycle), as illustrated in FIGS. 4 and 13 and input of a patient ID, as illustrated in FIGS. 5*a*, 5*b*, and 14. Specifically, the patient identification information can be entered for a new cycle from the screen shown in FIG. 5*a* if it is a new cycle, or patient I.D. can be selected using screen FIG. 5*b* if it is a continuing cycle. The physician may next select the path to find the initial dose or go to the rest of the cycle using these screens.

Figure 6:
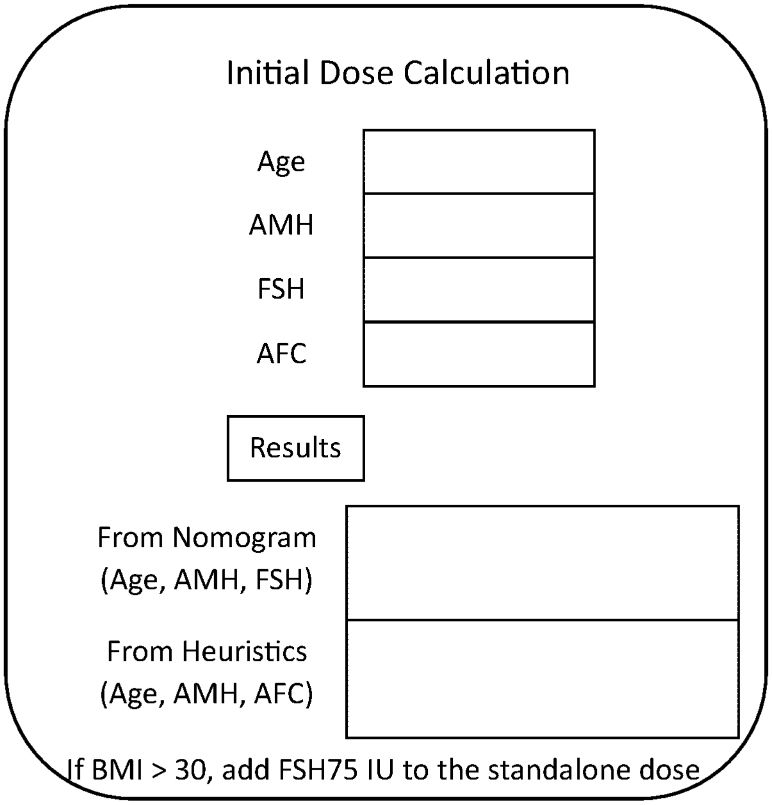
FIG. 6 illustrates an initial dose calculations screen for a decision support tool for determining personalized drug dosage profiles for patients in an embodiment of the present invention.
Figure 15:
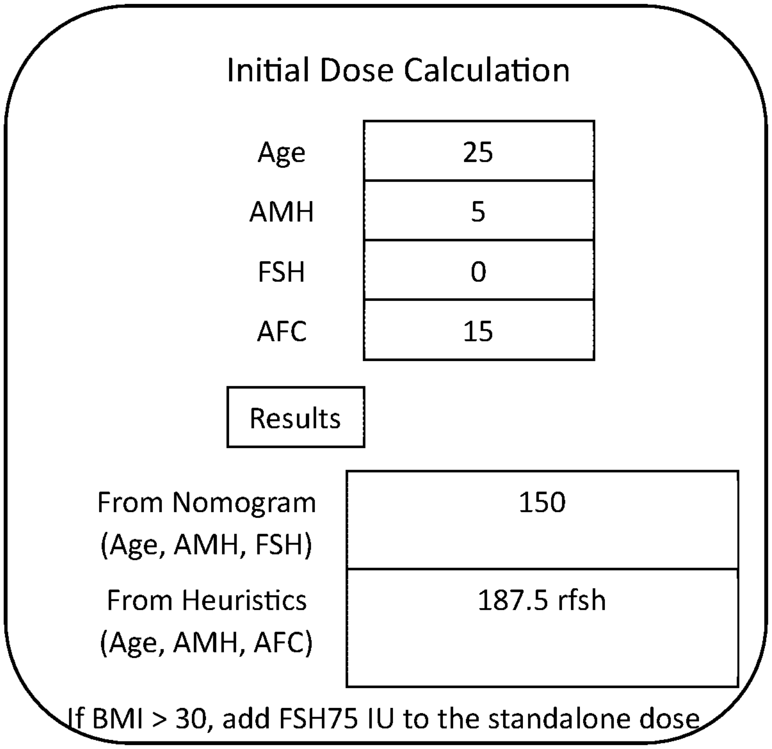
FIG. 15 illustrates an exemplary initial dose calculation screen for a decision support tool for determining a personalized drug dosage profile for a patient in an embodiment of the present invention.

The physician may then optionally use the initial dosage calculator (as shown in FIG. 1) to determine a first day dose determination (via step 14), either using a nomogram consisting of Age, AMH, and FSH data from the patient (via step 16) or, alternatively, heuristics data consisting of Age, AMH, and AFC (via step 18). An example initial dosage calculator is also illustrated in FIGS. 6 and 15. However, the physician can decide on their own initial dose without using the calculator provided by the invention and go to the next steps directly.

Figure 7:
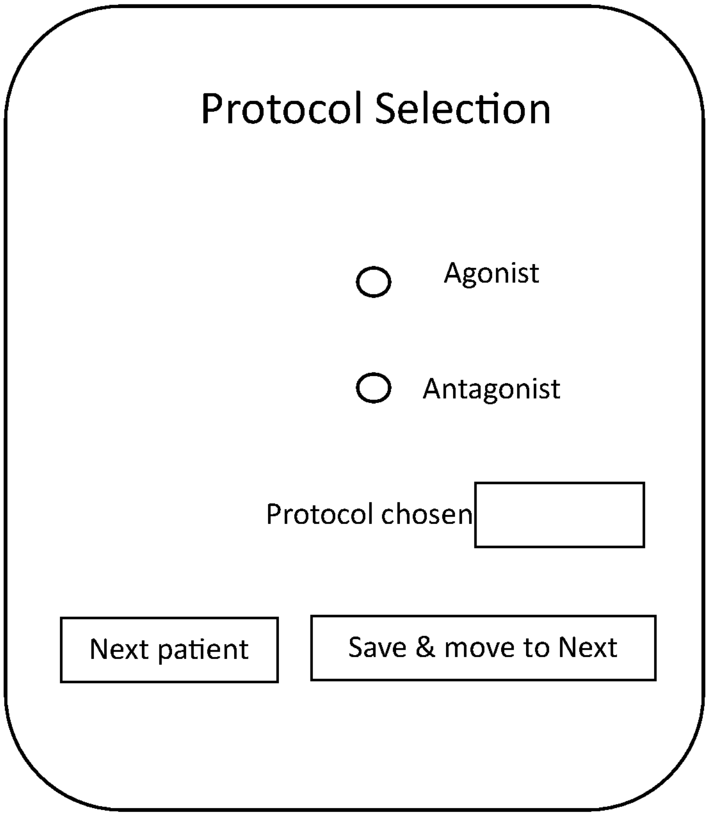
FIG. 7 illustrates a protocol selection screen for a decision support tool for determining personalized drug dosage profiles for patients in an embodiment of the present invention.
Figure 16:
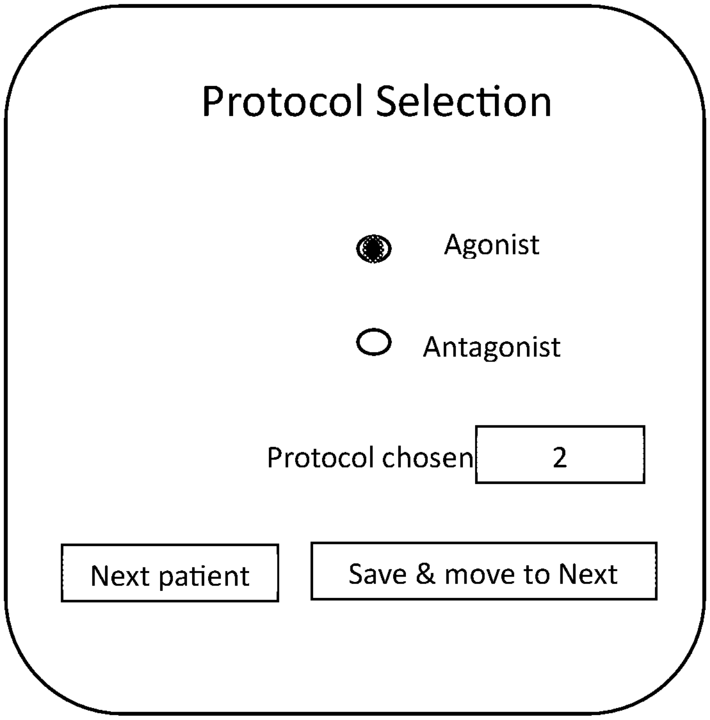
FIG. 16 illustrates an exemplary protocol selection screen for a decision support tool for determining a personalized drug dosage profile for a patient in an embodiment of the present invention.

An appropriate protocol may then be chosen for that patient (via step 20) specifically allowing a user to select whether the protocol is for an "agonist" or an "antagonist." Example screens showing the protocol selection are illustrated in FIGS. 7 and 16.

Figure 8:
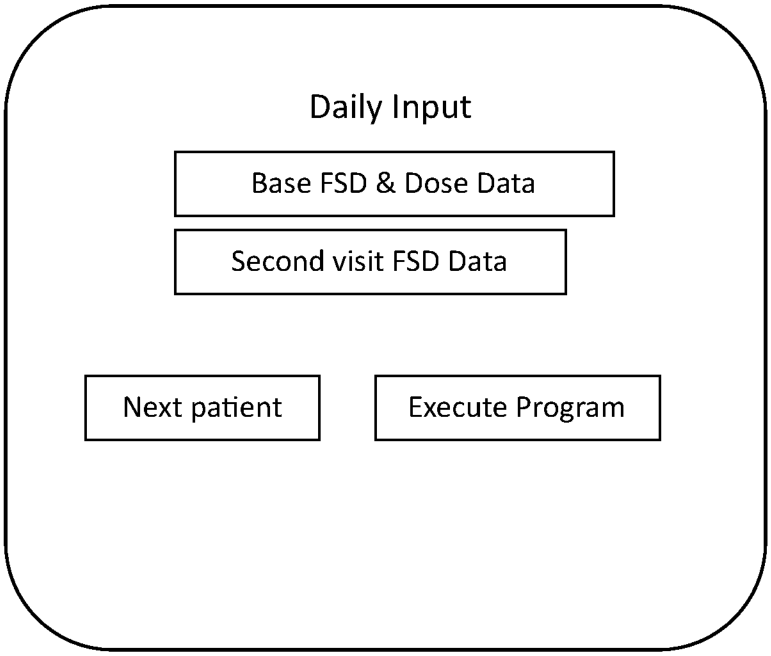
FIG. 8 illustrates a daily input data screen for a decision support tool for determining personalized drug dosage profiles for patients in an embodiment of the present invention.
Figure 9:
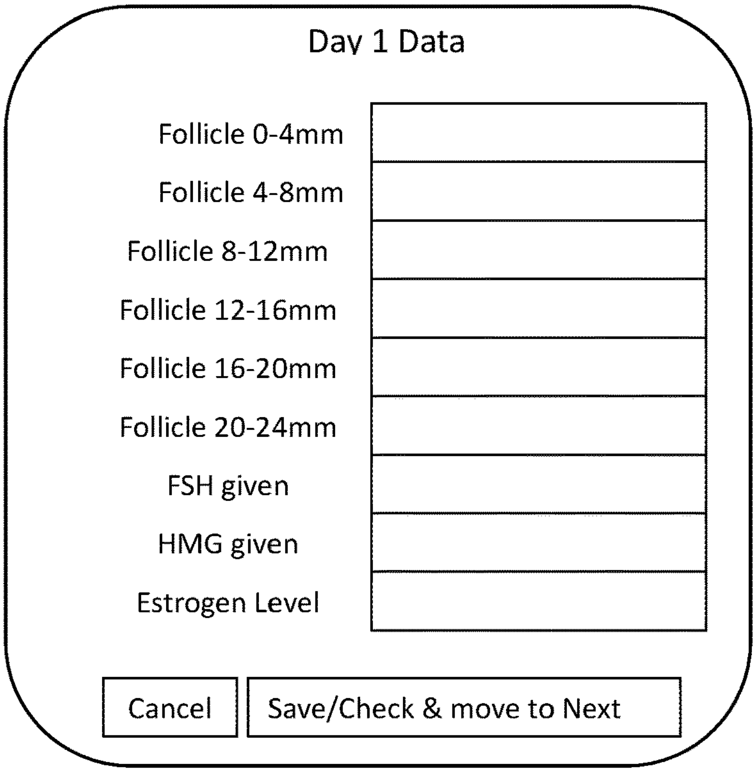
FIG. 9 illustrates base/first day follicle size distribution (FSD) and dosage input screen for a decision support tool for determining personalized drug dosage profiles for patients in an embodiment of the present invention.
Figure 17:
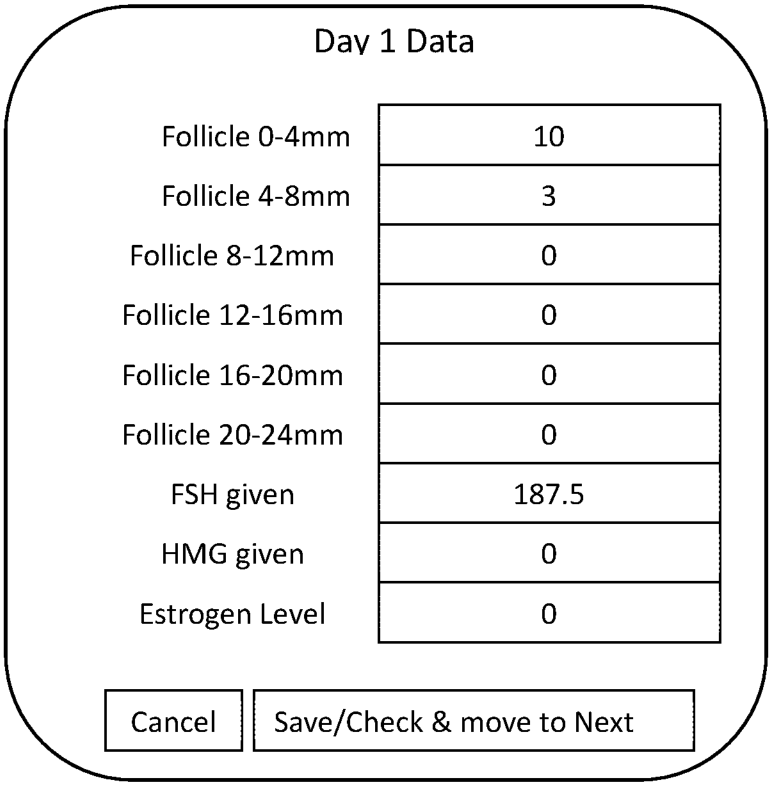
FIG. 17 illustrates an exemplary first day data screen for a decision support tool for determining a personalized drug dosage profile for a patient in an embodiment of the present invention.

FIG. 8 illustrates an option for the user to enter information concerning either initial follicular size distribution (FSD) data or second visit FSD data. If information concerning a new cycle is selected in the signup or sign-in screen, described above, the base FSD data (i.e., the follicular size distribution before first day of dosage) may be obtained using an apparatus configured to obtain FSD data, such as, for example, an ultrasound machine. The base FSD data and the initial hormone dosage may then be input into the system via step 22. Exemplary screens showing the input of base follicular size distribution data and initial hormone dosage is illustrated in FIGS. 9 and 17. If estrogen levels are measured, then that input may also be entered. If estrogen level is not available, then zero data may be given for estrogen. For example, as illustrated in FIG. 9, ultrasound data for follicle size distribution in terms of various bins (e.g., 0-4 mm, 4-8 mm, and so on), and the initial dose is given to the patient for base or first day. This dosage can be pure FSH, pure HMG, or a combination of FSH and HMG. As noted above, if estrogen level data is available, that can also be provided.

Figure 10:
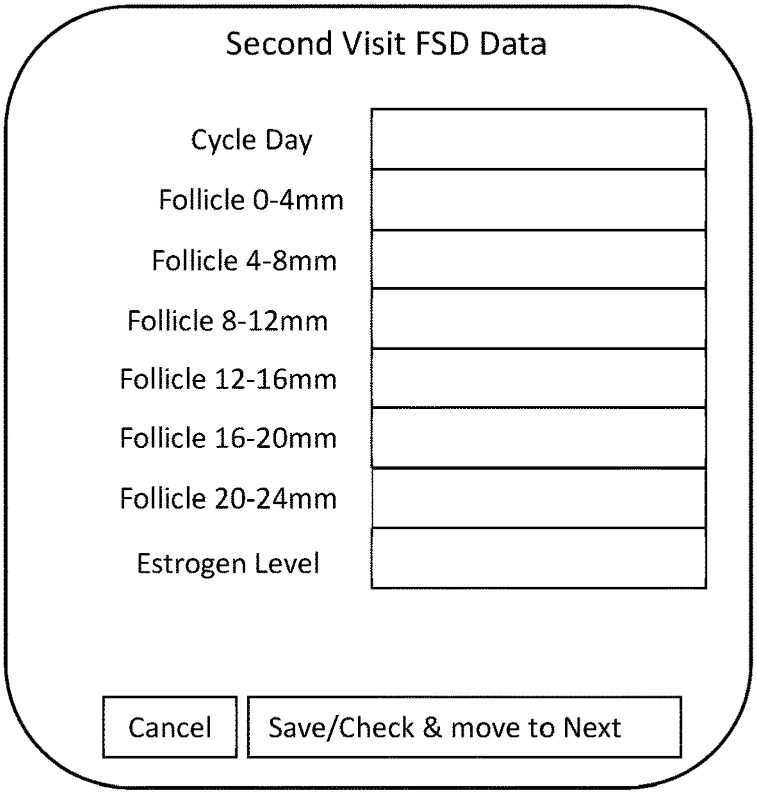
FIG. 10 illustrates a second visit follicle size distribution (FSD) input screen for a decision support tool for determining personalized drug dosage profiles for patients in an embodiment of the present invention.
Figure 18:
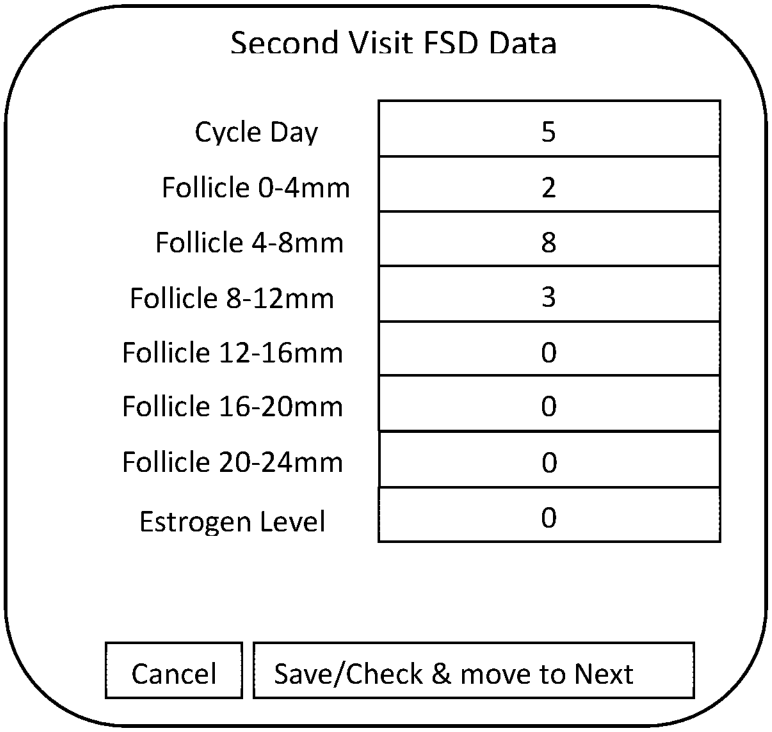
FIG. 18 illustrates an exemplary second day data screen for a decision support tool for determining a personalized drug dosage profile for a patient in an embodiment of the present invention.

The initial hormone (FSH & HMG) dose may continue until the patient comes for the second visit. This can be either on the fourth, fifth or sixth day. At the second visit, FSD data found for that day is measured via the apparatus configured to obtain the FSD data (such as, for example, the ultrasound machine) to the tool of the present invention via step 24. Exemplary screens showing the input of second visit FSD data is illustrated in FIGS. 10 and 18. Again, if estrogen levels are measured on the second visit, this information may also be entered.

The present invention utilizes optimal control theory to develop a personalized differential-algebraic equations-based model for that patient using the entered FSD data and initial hormone dosage information. Specifically, optimal control theory provides a series of differential calculations that are used to obtain the optimal daily dosage for the rest of the cycle for that patient. Alternatively, the specific results of the present invention may also be obtained using any other manner apparent to one of ordinary skill in the art, such as via machine learning, such as artificial intelligence technology, using, for example, brute force to obtain results without the use of optimal control theory and/or the series of differential calculations to obtain the optimal daily dosage and trigger day data.

Figure 11:
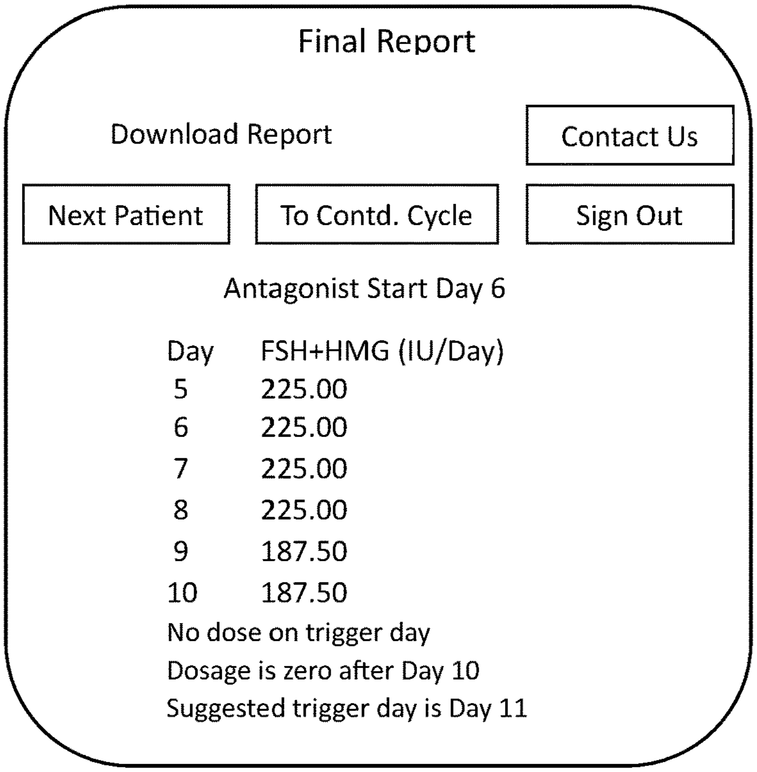
FIG. 11 illustrates a program execution and downloading report screen for a decision support tool for determining personalized drug dosage profiles for patients in an embodiment of the present invention.
Figure 19:
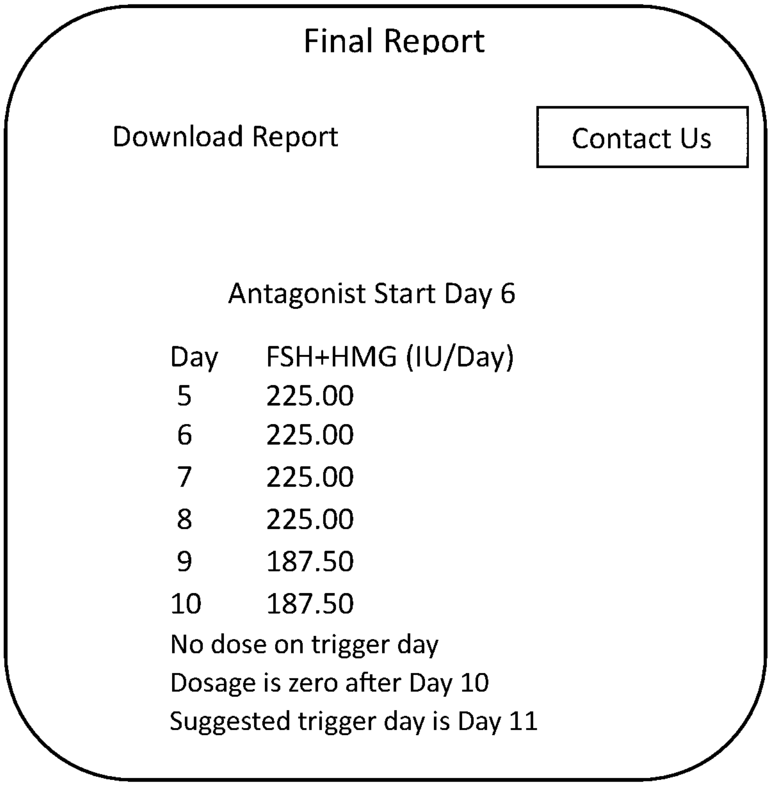
FIG. 19 illustrates an exemplary program execution and partial results screen for a decision support tool for determining a personalized drug dosage profile for a patient in an embodiment of the present invention.

Based on a projected daily follicular size distribution obtained by the model and optimization protocol generated by the optimal control theory calculations (or via any other method, as described above), the day to start antagonist, if antagonist protocol is used, and the trigger day of the cycle may be determined and presented to the user, as illustrated in FIGS. 11 and 19. On the trigger day, for example, no dosage is given.

Finally, the physician can download a full detailed report via step 26 which provides input data, optimal daily drug dosage for the complete cycle 28, estrogen levels (if the input is provided) for the complete cycle 30, and projected follicle size distribution. As noted above, the detailed report may further provide the antagonist start day (if antagonist protocol is selected) as well as the trigger day 32. Exemplary screens illustrated obtaining and/or downloading the detailed report are illustrated in FIG. 20.

EXAMPLE

FIGS. 12 to 20 present a detailed example of inputs and outputs for a patient. For example, as illustrated in FIG. 15, initial dose calculation data may be determined by, for example, entering the age, AMH, FSH, and/or AFC data and calculating initial doses based on the information. Moreover, FIG. 16 illustrates, in an exemplary embodiment, selection of an "antagonist" protocol. Using an ultrasound machine, follicular distribution data may be determined and entered, as illustrated in FIG. 17, which shows 10 follicles of 0-4 mm, 3 follicles of 4-8 mm, 0 follicles of 8-12 mm, 0 follicles of 12-16 mm, 0 follicles of 16-20 mm, and 0 follicles of 20-24 mm. Moreover, initial hormone dosage may be provided, either calculated via the initial hormone dose calculator, as described herein, or in another manner. And, of course, if an estrogen level is measured, this may also be entered.

Four, five or six days later, the patient may be seen for a second visit and second visit FSD data may be measured, via an ultrasound machine, and entered into the tool of the present invention. As illustrated in FIG. 18, the cycle day (5) after the first day is entered, followed by follicular size distribution data measured on the cycle day. In the example shown in FIG. 18, the ultrasound showed 2 follicles of 0-4 mm, 8 follicles of 4-8 mm, 3 follicles of 8-12 mm, 0 follicles of 12-16 mm, 0 follicles of 16-20 mm, and 0 follicles of 20-24 mm. Again, if measured, the estrogen level of the patient may be entered.

Upon entry, the tool may calculate the optimized daily hormone dosage and trigger day based on the entered data in a partial report, illustrated in FIG. 19. As illustrated in FIG. 19, starting on days 5, 6, 7, and 8 after the first day measurements, 225.00 IU/day of FSH+HHG hormone dosages were calculated, and on days 9 and 10 after the first day, 187.50 IU/day of FSH+HHG hormones dosages were calculated. The suggested trigger day is presented as day 11 and no dosage of hormones is indicated as presented for that day and beyond.

As illustrated in FIG. 20, the detailed report may illustrate specific calculated information, such as the information provided in the partial report, illustrated in FIG. 19, as well as reported and model follicular size distribution data on the first visit day, the second visit day, as well as all days of the cycle beyond the second visit day. As shown in FIG. 20, all follicles are estimated to have a size distribution between 20-24 mm by day 12, thereby providing the day showing the superovulation stage to provide the best results for harvesting eggs for use in vitro fertilization.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

I claim:

1. A method for facilitating an optimized and personalized drug treatment for in vitro fertilization (IVF) patients comprising the steps of:

providing an ultrasound apparatus configured to identify and measure follicle sizes in an IVF patient;

obtaining first follicle size distribution data of the IVF patient using the apparatus at a first time;

determining an initial hormone dosage for administering to the IVF patient;

administering the initial hormone dosage to the IVF patient until a second time;

obtaining second follicle size distribution data of the IVF patient using the ultrasound apparatus configured to identify and measure follicle sizes in the IVF patient at the second time;

providing a decision support tool comprising a software application configured to operate on a computing device, wherein the decision support tool is configured to calculate an optimized drug treatment plan for the IVF patient;

entering the first follicle size distribution data of the IVF patient, second follicle size distribution data of the IVF patient, and the initial hormone dosage administered to the IVF patient at the first time;

calculating the optimal daily hormone dosage for the IVF patient using the decision support tool, wherein the decision support tool uses optimal control theory comprising differential-algebraic equations using the first and the second follicle size distribution data of the patient and information about the initial hormone dosage; and administering the optimal daily hormone dosage to the IVF patient for a cycle of IVF treatment.

2. The method of claim 1 wherein determining the initial hormone dosage for administering to the IVF patient is determined using the decision support tool.

3. The method of claim 2 wherein the initial hormone dosage for administering to the IVF patient is based on an age of the IVF patient, anti-mullerian hormone (AMH) data of the IVF patient, and follicle stimulating hormone (FSH) data of the IVF patient.

4. The method of claim 3 wherein the initial hormone dosage is calculated using a nomogram.

5. The method of claim 2 wherein the initial hormone dosage for administering to the IVF patient is based on an age of the IVF patient, anti-mullerian hormone (AMH) data of the IVF patient, and antral follicle count (AFC) data of the IVF patient.

6. The method of claim 5 wherein the initial hormone data is calculated based on heuristics.

7. The method of claim 1 wherein the second time is between about 4 days and 6 days after the first time.

8. The method of claim 1 wherein the optimal daily dosage is determined for the IVF patient for the cycle of IVF treatment.

9. The method of claim 1 wherein the optimal daily hormone dosage comprises a hormone selected from the group of follicle stimulating hormone (FSH), human menopausal gonadotropins (HMG), and a combination of FSH and HMG.

10. The method of claim 9 wherein the decision support tool further calculates an antagonist start day.

11. The method of claim 1 wherein the decision support tool further calculates estrogen levels for each day of the cycle.

12. The method of claim 1 wherein the decision support tool further calculates expected daily follicle sizes for the cycle.

13. The method of claim 1 wherein the decision support tool further calculates a trigger day for the IVF patient within the cycle.

* * * * *